US012752030B2

(12) United States Patent
Deflorian et al.

(10) Patent No.: US 12,752,030 B2
(45) Date of Patent: Oct. 6, 2026

(54) DEVICE FOR DIFFUSING VOLATILE SUBSTANCES AND METHOD FOR ITS MANUFACTURING

(71) Applicant: ZOBELE HOLDING, S.P.A., Trento (IT)

(72) Inventors: Stefano Deflorian, Trento (IT); Alessio Dalser, Trento (IT); Stefano Mantovan, Trento (IT)

(73) Assignee: ZOBELE HOLDING, S.P.A., Trento (IT)

( * ) Notice: Subject to any disclaimer, the term of this patent is extended or adjusted under 35 U.S.C. 154(b) by 1224 days.

(21) Appl. No.: 17/046,542

(22) PCT Filed: Apr. 10, 2019

(86) PCT No.: PCT/EP2019/059069
§ 371 (c)(1),
(2) Date: Oct. 9, 2020

(87) PCT Pub. No.: WO2019/197458
PCT Pub. Date: Oct. 17, 2019

(65) Prior Publication Data
US 2021/0154349 A1 May 27, 2021

(30) Foreign Application Priority Data
Apr. 12, 2018 (EP) .................................... 18166958

(51) Int. Cl.
*A61L 9/04* (2006.01)
*B32B 3/26* (2006.01)
(Continued)

(52) U.S. Cl.
CPC .............. *A61L 9/042* (2013.01); *B32B 3/266* (2013.01); *B32B 27/10* (2013.01); *B32B 27/32* (2013.01);
(Continued)

(58) Field of Classification Search
CPC ......... A61L 9/042; B32B 3/266; B32B 27/10; B32B 27/32; B32B 27/36; B32B 27/06; B32B 27/24
(Continued)

(56) References Cited

U.S. PATENT DOCUMENTS 3,685,734 A * 8/1972 Paciorek ................ B32B 27/08 428/905
4,094,119 A * 6/1978 Sullivan .................... A61L 9/12 156/290
(Continued)

FOREIGN PATENT DOCUMENTS

WO WO94/27646 12/1994
WO WO-9735626 A1 * 10/1997 .......... A01M 1/2055
WO WO-2006056762 A1 * 6/2006 ............ A61L 9/037

OTHER PUBLICATIONS

International Search Report and Written Opinion dated Jul. 9, 2019 from PCT/EP2019/059069.

*Primary Examiner* — Kevin Edward Schwartz
(74) *Attorney, Agent, or Firm* — Sandberg Phoenix & von Gontard, P.C.

(57) ABSTRACT

The device (1) comprises a substrate (2) impregnated with volatile substances and a first film (3) that is impermeable to the volatile substances applied to one face of the substrate (2) and a second film (4) provided with a plurality of holes (5) applied to the other face of the substrate (2).
The method for manufacturing said device 1 comprises the following steps: applying a first film (3) to a face of the substrate (1); impregnating the substrate (1) by depositing the volatile substances on the face of the substrate (1) that is not coated with the first film (3); leaving the volatile substances to fully impregnate the substrate (1); and applying a second film (4) provided with a plurality of holes (5) to the other face of the substrate (1).
(Continued)

The device permits a more continuous diffusion of the volatile substances along time.

6 Claims, 1 Drawing Sheet

(51) Int. Cl.

| | |
|---|---|
| ***B32B 27/10*** | (2006.01) |
| ***B32B 27/32*** | (2006.01) |
| ***B32B 27/36*** | (2006.01) |
| ***B32B 37/06*** | (2006.01) |
| ***B32B 37/24*** | (2006.01) |

(52) U.S. Cl.
CPC .............. *B32B 27/36* (2013.01); *B32B 37/06* (2013.01); *B32B 37/24* (2013.01); *B32B 2037/243* (2013.01); *B32B 2255/12* (2013.01); *B32B 2255/26* (2013.01); *B32B 2260/028* (2013.01); *B32B 2260/04* (2013.01); *B32B 2307/31* (2013.01)

(58) Field of Classification Search
USPC ............................................................ 239/56
See application file for complete search history.

(56) References Cited

U.S. PATENT DOCUMENTS 4,158,440 A * 6/1979 Sullivan .................... A61L 9/12 239/6
4,515,703 A * 5/1985 Haq .................... C11D 17/049 510/159
4,529,124 A 7/1985 Sullivan et al.
4,655,767 A * 4/1987 Woodard ............. A61K 9/7069 428/156
4,874,129 A * 10/1989 DiSapio ............. A45D 40/0087 239/36
5,071,704 A * 12/1991 Fischel-Ghodsian ..... A61L 9/12 428/905
5,395,047 A * 3/1995 Pendergrass, Jr. ......... A61L 9/12 428/905
5,885,701 A * 3/1999 Berman .................. B32B 15/20 424/59
5,899,382 A * 5/1999 Hayes ....................... A61L 9/12 239/57
6,162,454 A * 12/2000 Ahr ......................... A61L 9/127 424/405
6,554,887 B1 * 4/2003 Inglis ...................... A01M 1/14 239/57
6,695,272 B1 * 2/2004 Bomgaars ............ A47G 23/032 248/346.11
8,763,805 B2 * 7/2014 Greenland ................ B32B 7/12 206/460
8,968,647 B2 3/2015 Fischer et al.
11,167,055 B2 * 11/2021 McKay ................... A61L 9/013
2003/0049394 A1 * 3/2003 Porchia ..................... A61L 9/12 428/40.1
2007/0031463 A1 * 2/2007 Fotinos .................. A01N 25/18 424/443
2014/0109329 A1 * 4/2014 Gummow ............... B32B 27/12 15/104.93
2014/0166774 A1 * 6/2014 Morhain ................... A61L 9/12 239/34
2014/0193295 A1 * 7/2014 Fischer ..................... A61L 9/12 422/4
2017/0266333 A1 * 9/2017 McKay ................... A61L 9/012
2020/0069832 A1 * 3/2020 Santini ...................... A61L 9/12

* cited by examiner

DEVICE FOR DIFFUSING VOLATILE SUBSTANCES AND METHOD FOR ITS MANUFACTURING

The present invention refers to a device for diffusing volatile substances, comprising a substrate impregnated with said volatile substances. The present invention also refers to a method for manufacturing a device for diffusing volatile substances.

BACKGROUND OF THE INVENTION

Impregnated carton with volatile substance are known for years. The simplest but still most popular application of this kind of product are car air fresheners consisting of an impregnated carton with an aesthetical artwork, impregnated with a fragrance and that is hanging from the rear mirror of the car. The main advantage of this kind of product is the cost.

Another advantage of the simple cellulosic support is that it is quite easy to manufacture, as the cellulose is quite absorbent. The amount of fragrance to be impregnated is simply put on the cellulose in horizontal position and after some seconds, is completely absorbed by the cellulose and then packed in an impermeable plastic film.

The olfactive performance is taking advantage of the generosity of the cellulose to release fragrance, but also presents the limitation of any open system that is that the high volatility components of the fragrance are released extremely fast and the low volatility remains longer. This way the smell of the device is progressively decaying and changing in its hedonic notes.

Several intends have been done to try to improve the performance with a limited cost increase. An example is U.S. Pat. No. 8,968,647B2 where a permeable membrane is applied on the top of the substrate, in order to control (reduce) the evaporation. Nevertheless, these improved versions are not fully satisfactory. On one side, the use of a semipermeable membrane does not only delay the release, it also filters the components of the fragrance, leading thus in a different fragrance.

Also, the presence of a plastic layer (impermeable or permeable) covering partially or completely the cardboard limits the possibility to impregnate the substrate with the fragrance. Even if the cardboard is only partially covered by the film, the quantity of free cardboard where to deposit the liquid will be reduced that definitively leads to a reduction of the impregnation speed and thus of the productivity.

Therefore, one purpose of the present invention is to provide a device for diffusing volatile substances achieving a more continuous release and a method for manufacturing such device.

DESCRIPTION OF THE INVENTION

With the device for diffusing volatile substances according to the present invention it is possible to solve said drawbacks, providing other advantages that are described below.

The device for diffusing volatile substances according to the present invention comprises a substrate impregnated with volatile substances, and it is characterized in that the device comprises a first film that is impermeable to the volatile substances applied to one face of the substrate and a second film provided with a plurality of holes applied to the other face of the substrate.

Preferably, said second film is impermeable to said volatile substances, even though it could also be semipermeable to said volatile substances.

According to a preferred embodiment, the diameter of the holes is between 0.5 cm and 2 cm, and the separation between two adjacent holes is less than the double of the diameter of the holes.

Preferably, the first film and the second film have a thickness between 20 and 100 microns, the substrate is made from cardboard, and the substrate has a thickness between 1 and 2 mm.

According to a second aspect, the invention also refers to a method for manufacturing a device for diffusing volatile substances according to any of the previous claims, said device comprising a substrate, that is characterized in that the method comprises the following steps:

- applying a first film to a face of the substrate;
- impregnating the substrate by depositing the volatile substances on the face of the substrate that is not coated with the first film;
- leaving the volatile substances to fully impregnate the substrate; and
- applying a second film provided with a plurality of holes to the other face of the substrate.

Preferably, the method also comprises, after the application of the second film, the step of sealing the second film by heat sealing, so that the second film is fixed to the substrate.

For preventing the undesired diffusion of the volatile substances during the manufacturing of the device, the method also comprises, during the application of the second film, using a liner covering the second film.

The liner can be a film that is placed between the top film and the welding tool during welding, and then is only in contact with the product during the welding step.

Alternatively, the liner can be a continuous film on which the top film is placed before to enter in the welding station Still alternatively, the liner and the top film are laminated together off line, as two continuous layers. The holes in the top film are made by laser cutting, remaining the plastic film of the inner of the holes on the liner, welding the multilayer liner/top film without applying pressure and heat on the areas corresponding to the inner of the holes, then removing the liner, leaving the top film on top of the substrate but removing the inner of the holes together with the liner. This last operation of separating liner from the top film can be done during the production process or by the consumer.

The device for diffusing volatile substances according to the present invention permits a more continuous diffusion of the volatile substances along time.

BRIEF DESCRIPTION OF THE DRAWINGS

For a better understanding the above explanation and for the sole purpose of providing an example, some non-limiting drawings are included that schematically depict a practical embodiment.

DESCRIPTION OF A PREFERRED EMBODIMENT

Figure 1:
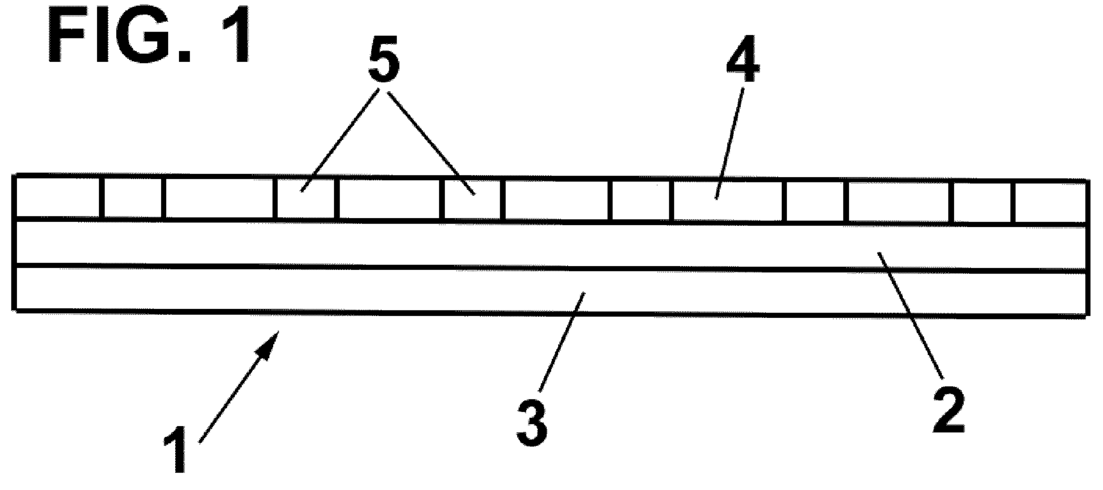
FIG. 1 is a cross-section view of the device for diffusing volatiles substances according to the present invention.
Figure 2:
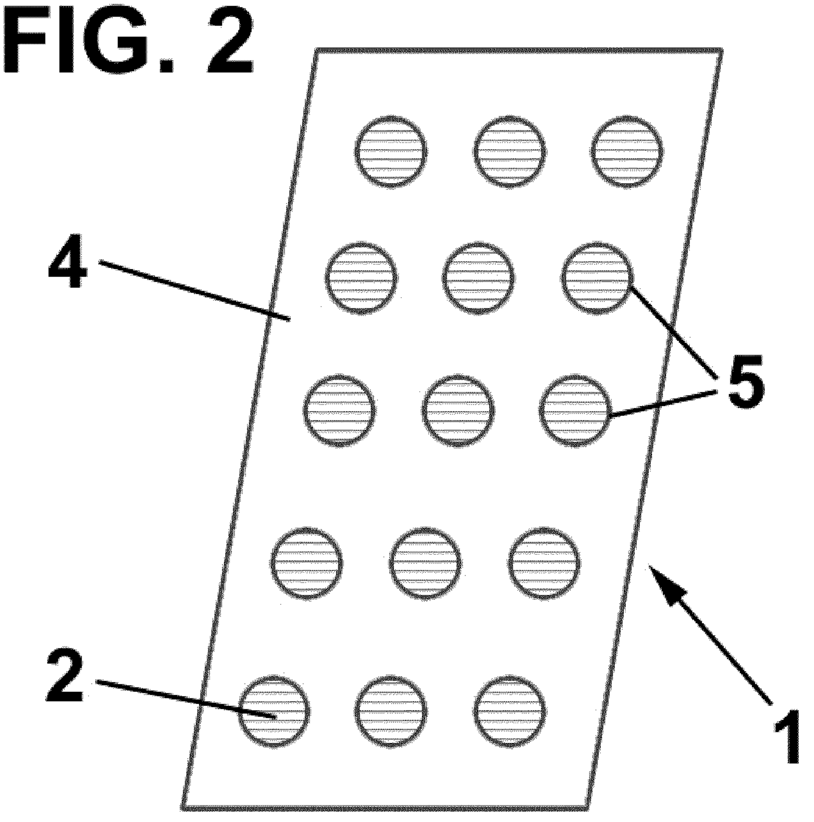
FIG. 2 is a frontal view of the device for diffusing volatiles substances according to the present invention.

The present invention refers to a device for diffusing volatile substances, indicated generally by numeral reference 1, comprising a substrate 2 impregnated with volatile substances, covered on one side by a first film 3 and on the other side by a second film 4 in which a plurality of holes 5 has been done.

According to a preferred embodiment, the substrate 2 is a cardboard substrate, the first film 3 is an impermeable plastic film and the second film 4 is preferably also impermeable to fragrances, although a permeable film could also be used, assuming this will lead to a lower performance results, as the volatile substances will be filtered in the area where it is covered by this permeable film.

The evaporation will take place mainly from the holes 5 done in the second film 4, as we consider the evaporation of the outer perimeter of the substrate 2 (that is not covered by any film) as very low and limited to the first hours of the product.

The part of the substrate 2 that is not covered by the first or second films 3, 4 will behave like a typical cardboard substrate 2 without any film and then release the volatile substance without any limit, and so with the decompensation of fragrance components as described above.

The part of the substrate 2 that is covered by the first or second films 3, 4 will not contribute directly to the evaporation, but will feed progressively the not covered areas with fresh doses of the volatile substance that will evaporate from there.

The resulting evaporation will have an initial lower evaporation rate in comparison with a standard impregnated substrate with the same dimensions but followed by a lower decay in weight loss per hour.

If we consider a fragrance, the initial lower evaporation rate can be compensated by using a fragrance with a higher volatility.

The size of the holes 5 in the second film 4 is preferably in the range from 0.5 to 2 cm, and more preferably around 1 cm.

The distance between two holes preferably remains below the double of the size of the holes 5 and also below 3 cm.

The thickness of the substrate 2 is preferably from 1 to 2 mm, more preferably, 1.5 mm.

The thickness of the first and second films 3, 4, that are preferably of the same material, is between 20 to 100 microns. The first and second films 3, 4 are preferably multilayer films, with a barrier material, for example PET, maybe complemented by an EVOGH layer, and a heat sealing layer, preferably made of polyethylene, polypropylene, or ionomer resin.

The device for diffusing volatile substances 1 according to the present invention is packed in an impermeable envelope (not shown in the drawings) that avoid any fragrance loss before a first use.

The present invention also refers to a method for manufacturing a device for diffusing volatile substances as described previously.

According to a preferred embodiment, this method comprises the following steps:

- applying the first film 3 to a face of the substrate 1;
- impregnating the substrate 1 by depositing the volatile substances on the side of the substrate 1 that is not coated with the first film 3;
- leaving the volatile substances to fully impregnate the substrate 1;
- applying the second film 4 to the other face of the substrate 1;
- sealing the second film 4 by heat sealing, so that the second film 4 is fixed to the fibers of the substrate 1.

The heat necessary to seal the second film 4 will influence the volatile substances. On one side, it can provoke unwanted evaporation of part of the volatile substances; on the other side, it can degrade part of the volatile substances.

In the case of an air freshener, even a small portion of the substance degraded can provoke a significant change in the olfactive note.

For this reason, it is preferred to apply the second film 4 with a liner that covers the whole second film 4, in order the volatile substances are never directly exposed to the heating plate of the sealing tool, and there is no exit for the volatile substances to evaporate from the second film 4 before the liner is removed.

The liner consists in a plastic film that is not sensitive to the temperature used during the sealing of the second film 4 on the substrate 1. Preferably, the liner is made of a polyester film with a layer between the liner and the second film 4 made of polyurethane resin.

Even though reference has been made to a specific embodiment of the invention, it is obvious for a person skilled in the art that the device described herein is susceptible to numerous variations and modifications, and that all the details mentioned can be substituted for other technically equivalent ones without departing from the scope of protection defined by the attached claims.

The invention claimed is:

1. A device for diffusing substances comprising a substrate with fibers impregnated with the substances, the device comprising a first film that is impermeable to the substances applied to one face of the substrate and a second film provided with a plurality of holes applied to an other face of the substrate, wherein the second film is heat sealed, so that the second film is fixed to the fibers of the substrate, wherein the second film is impermeable or semipermeable to the substances, wherein a diameter of the holes is in a range of 0.5 cm to 2 cm, wherein the first film and the second film have a thickness between 20 microns and 100 microns, wherein the substrate has a thickness between 1 mm and 2 mm, wherein the substrate is made from cardboard, and wherein the first film and the second film together define a multilayer film.

2. The device for diffusing substances according to claim 1, wherein a separation between two adjacent holes of the plurality of holes is less than double of the diameter of the holes.

3. A device for diffusing substances, the device consisting of:

- a substrate with fibers, the substrate having a first surface and a second surface on opposite sides of the substrate;
- a substance impregnating the substrate;
- a first film applied to the first surface of the substrate, the first film covers the first surface of the substrate, the first film is impermeable to the substance impregnating the substrate;
- a second film applied to the second surface of the substrate, the second film covers the second surface of the substrate,
- the second film having a plurality of holes through the second film;
- and the second film is heat sealed to the second surface of the substrate and fixed to the fibers of the substrate; and
- wherein the second film is impermeable or semipermeable to the substances, wherein a diameter of the holes is in a range of 0.5 cm to 2 cm, wherein the first film and the second film have a thickness between 20 microns and 100 microns, wherein the substrate has a thickness between 1 mm and 2 mm, wherein the substrate is made from cardboard, and wherein the first film and the second film together define a multilayer film.

4. The device for diffusing substances according to claim 3, wherein:

adjacent holes of the plurality of holes through the second film are separated by a distance less than twice a diameter dimension of the adjacent holes.

5. A device for diffusing substances, the device consisting essentially of:

a substrate, the substrate having a first surface and a second surface on opposite sides of the substrate;

a substance impregnating the substrate;

a first film applied to the first surface of the substrate, wherein the first film covers the first surface of the substrate, wherein the first film is impermeable to the substance impregnating the substrate;

a second film applied to the second surface of the substrate, wherein the second film covers the second surface of the substrate, the second film is heat sealed to the second surface of the substrate and fixed to fibers of the substrate;

wherein the second film has a plurality of holes through the second film; and wherein the second film is impermeable or semipermeable to the substances, wherein a diameter of the holes is in a range of 0.5 cm to 2 cm, wherein the first film and the second film have a thickness between 20 microns and 100 microns, wherein the substrate has a thickness between 1 mm and 2 mm, wherein the substrate is made from cardboard, and wherein the first film and the second film together define a multilayer film.

6. The device for diffusing substances according to claim 5, wherein:

adjacent holes of the plurality of holes through the second film are separated by a distance less than twice a diameter dimension of the adjacent holes.

* * * * *